United States Patent [19]
Rueb et al.

[11] Patent Number: 5,089,042
[45] Date of Patent: Feb. 18, 1992

[54] N-PHENYLTETRAHYDROPHTHALIMIDE COMPOUNDS

[75] Inventors: Lothar Rueb, Speyer; Karl Eicken, Wachenheim; Barbara Schwalge, Ludwigshafen; Peter Plath, Frankenthal; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 511,940

[22] Filed: Apr. 16, 1990

Related U.S. Application Data

[63] Continuation of Ser. No. 279,518, Dec. 5, 1988, abandoned.

[30] Foreign Application Priority Data

Dec. 5, 1987 [DE] Fed. Rep. of Germany .... 3741273.6

[51] Int. Cl.$^5$ .................... A01N 43/34; A01N 43/36; A01N 43/38; C07D 209/48
[52] U.S. Cl. .......................................... 71/74; 71/95; 71/96; 548/513
[58] Field of Search ................ 71/74, 95, 96; 548/513

[56] References Cited

U.S. PATENT DOCUMENTS 3,772,334  11/1973  Teach ...................... 71/90

FOREIGN PATENT DOCUMENTS 0207894  1/1987  European Pat. Off. .
0289910  11/1988  European Pat. Off. ............ 548/513
87/07602  12/1987  World Int. Prop. O. .

Primary Examiner—Robert A. Wax
Assistant Examiner—F. Tsung
Attorney, Agent, or Firm—Oblon, Spivak, McClelland, Maier & Neustadt

[57] ABSTRACT

N-phenyltetrahydrophthalimides of the formula I

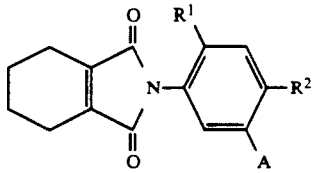

where $R^1$ is hydrogen or halogen, $R^2$ is halogen and A is a substituent of the formula

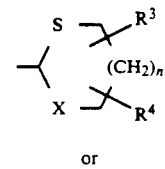

or

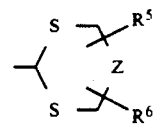

where X is oxygen or sulfur, n is zero or one, $R^3$ is hydrogen or $C_1$-$C_6$-alkoxycarbonyl or $C_1$-14 $C_3$-alkyl which is unsubstituted or substituted by halogen, cyano, hydroxyl, mercapto, $C_1$-$C_6$-alkoxycarbonyl, $C_1$-$C_4$-alkoxy, $C_1$-$C_4$-alkylthio, $C_3$-$C_6$-alkenyloxy, $C_3$-$C_6$-alkenylthio, $C_3$-$C_6$-alkynyloxy, $C_3$-$C_6$-alkynylthio or $C_1$-$C_4$-acyloxy, or is hydroxyl or carboxyl or is $C_1$-$C_4$-alkylthio-$C_1$- or $C_2$-alkyl or $C_1$-$C_4$-alkoxy-$C_1$- or -$C_2$-alkyl which is substituted in the alkyl ether or thioehter moiety by $C_1$-$C_6$-alkoxycarbonyl, $R^4$ is hydrogen or $C_1$-$C_3$-alkyl, Z is methyleneoxymethylene, methylenethiomethylene or ethenylene (—CH=CH—) and $R^5$ and $R^6$ are each hydrogen or $C_1$-$C_3$-alkyl, which are useful as herbicides, are prepared.

18 Claims, No Drawings

N-PHENYLTETRAHYDROPHTHALIMIDE COMPOUNDS

This application is a continuation of application Ser. No. 07/279,518, filed on Dec. 5, 1988, now abandoned.

N-aryl-substituted tetrahydrophthalimides having a herbicidal action are known. For example, European Patent 207,894 describes tetrahydrophthalimides of the formula I'

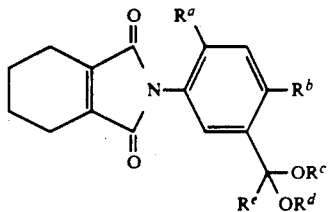

where the radicals have, for example, the following meanings:

$R^a$ and $R^b$ are identical or different and each denotes hydrogen or a halogen atom;

$R^c$ and $R^d$ together denote a substituted or unsubstituted $C_2$-$C_3$-alkylene bridge, and $R^e$ denotes, inter alia, hydrogen, cyano or $C_1$-$C_4$-alkyl.

However, the action of these compounds at low application rates is unsatisfactory.

The object of the invention was therefore, to provide N-phenyltetrahydrophthalimide compounds which have, at low application rates, a better herbicidal action on unwanted plants without damaging crop plants.

This object is achieved by tetrahydrophthalimides of the formula I

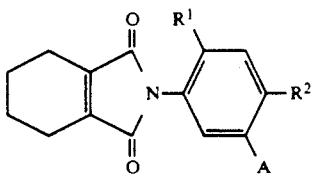

where $R^1$ is hydrogen or halogen, $R^2$ is halogen and A is a substituent of the formula

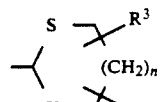

or

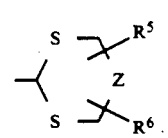

where X is oxygen or sulfur, n is zero or one, $R^3$ is hydrogen or $C_1$-$C_6$-alkoxycarbonyl or $C_1$-$C_3$-alkyl which is unsubstituted or substituted by halogen, cyano, hydroxyl, mercapto, $C_1$-$C_6$-alkoxycarbonyl, $C_1$-$C_4$-alkoxy, $C_1$-$C_4$-alkylthio, $C_3$-$C_6$-alkenyloxy, $C_3$-$C_6$-alkenylthio, $C_3$-$C_6$-alkynyloxy, $C_3$-$C_6$-alkynylthio or $C_1$-$C_4$-acyloxy, or is hydroxyl or carboxyl or is $C_1$-$C_4$-alkylthio-$C_1$- or -$C_2$-alkyl or $C_1$-$C_4$-alkoxy-$C_1$- or -$C_2$-alkyl which is substituted in the alkyl ether or thioether moiety by $C_1$-$C_6$-alkoxycarbonyl, $R^4$ is hydrogen or $C_1$-$C_3$-alkyl, Z is methyleneoxymethylene, methylenethiomethylene or ethenylene (—CH=CH—) and $R^5$ and $R^6$ are each hydrogen or $C_1$-$C_3$-alkyl, have an advantageous herbicidal action, particularly in the post-emergence method, and are selective with respect to a number of crops.

Halogen as used above is fluorine, chlorine or bromine, and halogen radicals $R^1$ are preferably fluorine and halogen radicals $R^2$ are preferably chlorine.

Alkyl (alone or as part of a substituent) includes branched or straight-chain radicals, e.g. methyl or ethyl, n-propyl and isopropyl.

Alkenyl and alkynyl may likewise be branched or straight-chain. Examples of alkenyl radicals in the formula I are allyl, 2-butenyl, 3-butenyl, 2-isobutenyl, 2-pentenyl, 3-pentenyl and 4-pentenyl, in particular allyl or 2-butenyl, alkynyl is, as a rule, propargyl, 2-butynyl, 3-butynyl or isomeric pentynyl radicals; however, alkynyl is preferably propargyl or 2- or 3-butynyl.

As a substituent of the general formula I, alkoxy is methoxy, ethoxy, n-propoxy, isopropoxy and the four isomeric butoxy radicals, in particular methoxy, ethoxy or isopropoxy. Examples of alkylthio in the formula I are n-propylthio, isopropylthio and n-butylthio, and in particular methylthio and ethylthio.

In the case of substitution in the thioacetal moiety, the formula I embraces enantiomers, diastereomers and their mixtures.

The compounds of the formula I can be considered as N-substituted tetrahydrophthalimides; accordingly, they are obtainable from 3,4,5,6-tetrahydrophthalic anhydride and an aniline of the formula V, for example in a solvent, at from 0° to 150° C., preferably from 20° to 100° C. Examples of suitable solvents are lower alkanoic acids, such as glacial acetic acid and propionic acid, and aprotic solvents, such as toluene and xylene, in the presence of acidic catalysts, such as aromatic sulfonic acids.

Preferred compounds I are those in which $R^1$ is hydrogen or fluorine, $R^2$ is chlorine and A is dithiane, dithiolane, oxathiolane or their substituted analogs.

The anilines of the formula V can be obtained, for example, by reducing an appropriately substituted nitrobenzene IV with a reducing agent, such as iron or a tin(II) salt.

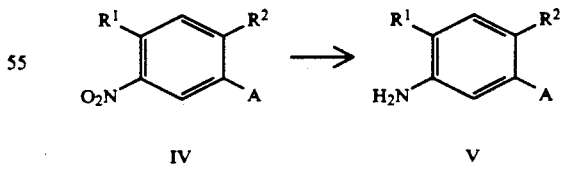

The reduction can also be carried out in the form of catalytic hydrogenation over a metal catalyst, such as platinum, palladium or Raney nickel, under relatively mild conditions.

The nitrobenzenes IV are obtainable by reacting a benzaldehyde II in a solvent with a dithiol or mercaptoalkanol of the formula IIIa or IIIb in the presence of an acid.

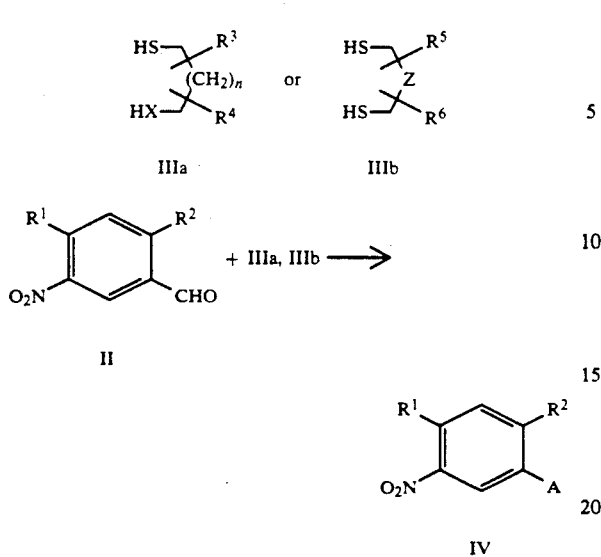

IIIa    IIIb

II + IIIa, IIIb →

IV

The recommended procedures given in the Examples below were used with appropriate modification of the starting compounds to obtain further compounds of the general formula I. The compounds are listed together with physical data in the Tables below. Compounds without such data can be obtained from corresponding substances in a similar manner. Because of their close structural relationship with the compounds prepared and investigated, they are expected to have a similar action.

EXAMPLE

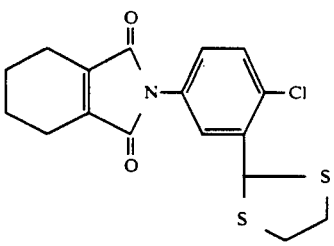

a) 9.9 g of ethane-1,2-dithiol are added to 18.6 g of 2-chloro-5-nitrobenzaldehyde and 0.5 g of p-toluenesulfonic acid in 250 ml of toluene, and the mixture is refluxed for 5 hours under a water separator. After the mixture has cooled, the solvent is removed, the residue is stirred with petroleum ether and the product is filtered off and dried. 25.5 g of 4-chloro-3-(1,3-dithiolan-2-yl)-nitrobenzene (mp. 130°-131° C.) are obtained.

b) 24.9 g of the above nitro compound are added a little at a time to a mixture of 15.9 g of iron powder in 50 ml of methanol and 75 ml of glacial acetic acid under reflux, and refluxing is continued for 2 hours. After the mixture has cooled, 250 ml of water are added and the solid is filtered off. The filtrate is extracted with 3 times 100 ml of ethyl acetate, the extracts are dried and evaporated down and the product is precipitated from petroleum ether, filtered off under suction and dried. 21.5 g of 4-chloro-3-(1,3-dithiolan-2-yl)-aniline (mp. 60°-63° C.) are obtained.

c) 11.6 g of the above aniline and 7.6 g of cyclohexene-1,2-dicarboxylic anhydride in 150 ml of glacial acetic acid are stirred for 2 days at room temperature, and the precipitate which separates out is filtered off, washed with water and petroleum ether and dried. 13 g of N-[4-chlorophenyl-3-(1,3-dithiolan-2-yl)]-3,4,5,6-tetrahydrophthalimide (mp. 155°-158° C.) (Table 1 No. 1.001) are obtained.

Other examples of active ingredients which can be synthesized using this principle are shown in Tables 1 to 5.

TABLE 1

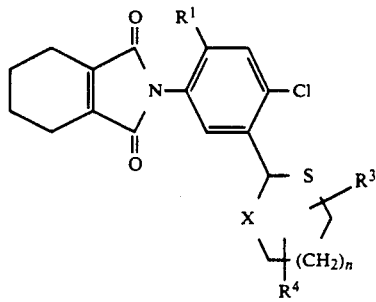

| No. | $R^1$ | $R^3$ | $R^4$ | n | X | mp. [°C.] |
|---|---|---|---|---|---|---|
| 1.001 | H | H | H | 0 | S | 155–158 |
| 1.002 | F | H | H | 0 | S | 160–161 |
| 1.003 | H | 4-$CH_3$ | H | 0 | S | 101–102 |
| 1.004 | F | 4-$CH_3$ | H | 0 | S | 138–139 |
| 1.005 | H | 4-$CH_2CH_3$ | H | 0 | S | |
| 1.006 | F | 4-$CH_2CH_3$ | H | 0 | S | |
| 1.007 | H | 4-$(CH_2)_2CH_3$ | H | 0 | S | |
| 1.008 | F | 4-$(CH_2)_2CH_3$ | H | 0 | S | |
| 1.009 | H | 4-$CH(CH_3)_2$ | H | 0 | S | |
| 1.010 | F | 4-$CH(CH_3)_2$ | H | 0 | S | |
| 1.011 | H | 4-$CH_2Cl$ | H | 0 | S | 109–110 |
| 1.012 | F | 4-$CH_2Cl$ | H | 0 | S | |
| 1.013 | H | 4-$CH_2Br$ | H | 0 | S | |
| 1.014 | F | 4-$CH_2Br$ | H | 0 | S | |
| 1.015 | H | 4-$CH_2CN$ | H | 0 | S | 82–84 |
| 1.016 | F | 4-$CH_2CN$ | H | 0 | S | |
| 1.017 | H | 4-$CH_2OH$ | H | 0 | S | 88–90 |
| 1.018 | F | 4-$CH_2OH$ | H | 0 | S | |
| 1.019 | H | 4-$CH_2SH$ | H | 0 | S | 96–97 |
| 1.020 | F | 4-$CH_2SH$ | H | 0 | S | |
| 1.021 | H | 4-$CH_2COOCH_3$ | H | 0 | S | |
| 1.022 | F | 4-$CH_2COOCH_3$ | H | 0 | S | |
| 1.023 | H | 4-$CH_2CO_2CH_2CH_3$ | H | 0 | S | |
| 1.024 | F | 4-$CH_2CO_2CH_2CH_3$ | H | 0 | S | |
| 1.025 | H | 4-$CH_2OCH_3$ | H | 0 | S | |
| 1.026 | F | 4-$CH_2OCH_3$ | H | 0 | S | |
| 1.027 | H | 4-$CH_2OCH_2CH_3$ | H | 0 | S | |
| 1.028 | F | 4-$CH_2OCH_2CH_3$ | H | 0 | S | |
| 1.029 | H | 4-$CH_2SCH_3$ | H | 0 | S | oil |
| 1.030 | F | 4-$CH_2SCH_3$ | H | 0 | S | |
| 1.031 | H | 4-$CH_2CH_2SCH_3$ | H | 0 | S | |
| 1.032 | F | 4-$CH_2CH_2SCH_3$ | H | 0 | S | |
| 1.033 | H | 4-$CH_2OCH_2CH=CH_2$ | H | 0 | S | |
| 1.034 | F | 4-$CH_2OCH_2CH=CH_2$ | H | 0 | S | |
| 1.035 | H | 4-$CH_2OCH_2C\equiv CH$ | H | 0 | S | |
| 1.036 | F | 4-$CH_2OCH_2C\equiv CH$ | H | 0 | S | |
| 1.037 | H | 4-$CH_2OCOCH_3$ | H | 0 | S | 80–81 |
| 1.038 | F | 4-$CH_2OCOCH_3$ | H | 0 | S | |
| 1.039 | H | 4-$CH_2OCOCH_2CH_3$ | H | 0 | S | |
| 1.040 | F | 4-$CH_2OCOCH_2CH_3$ | H | 0 | S | |
| 1.041 | H | 4-$CO_2CH_3$ | H | 0 | S | |
| 1.042 | F | 4-$CO_2CH_3$ | H | 0 | S | |
| 1.043 | H | 4-$CO_2CH_2CH_3$ | H | 0 | S | |
| 1.044 | F | 4-$CO_2CH_2CH_3$ | H | 0 | S | |
| 1.045 | H | 4-COOH | H | 0 | S | |
| 1.046 | F | 4-COOH | H | 0 | S | |
| 1.047 | H | 4-$CH_2SCH_2CO_2CH_3$ | H | 0 | S | oil |
| 1.048 | F | 4-$CH_2SCH_2CO_2CH_3$ | H | 0 | S | |
| 1.049 | H | 4-$CH_2SCH_2CO_2CH_2CH_3$ | H | 0 | S | |
| 1.050 | F | 4-$CH_2SCH_2CO_2CH_2CH_3$ | H | 0 | S | |
| 1.051 | H | 4-$CH_2OCH_2CO_2CH_3$ | H | 0 | S | |
| 1.052 | F | 4-$CH_2OCH_2CO_2CH_3$ | H | 0 | S | |
| 1.053 | H | 4-$CH_2OCH_2CO_2CH_2CH_3$ | H | 0 | S | |

TABLE 1-continued

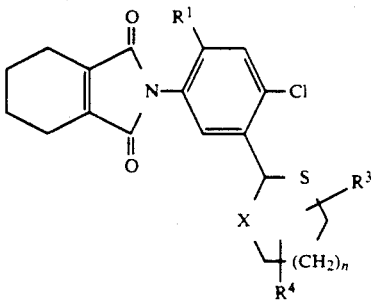

| No. | R¹ | R³ | R⁴ | n | X | mp. [°C.] |
|---|---|---|---|---|---|---|
| 1.054 | F | 4-CH₂OCH₂CO₂CH₂CH₃ | H | 0 | S | |
| 1.055 | H | 4-CH₃ | 5-CH₃ | 0 | S | |
| 1.056 | F | 4-CH₃ | 5-CH₃ | 0 | S | |
| 1.057 | H | 4-CH₂SCH₂CH=CH₂ | H | 0 | S | oil |
| 1.058 | F | 4-CH₂SCH₂CH=CH₂ | H | 0 | S | |
| 1.059 | H | 4-CH₂SCH₂C≡CH | H | 0 | S | oil |
| 1.060 | F | 4-CH₂SCH₂C≡CH | H | 0 | S | |
| 1.061 | H | 4-CH₂SCH(CH₃)CO₂CH₃ | H | 0 | S | oil |
| 1.062 | F | 4-CH₂SCH(CH₃)CO₂CH₃ | H | 0 | S | |

TABLE 2

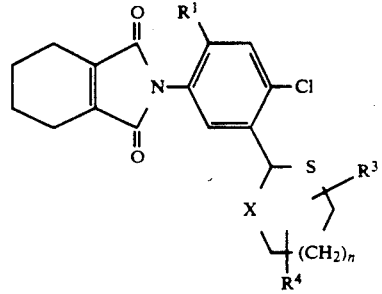

| No. | R¹ | R³ | R⁴ | n | X | mp. [°C.] |
|---|---|---|---|---|---|---|
| 2.001 | H | H | H | 0 | O | 141–142 |
| 2.002 | F | H | H | 0 | O | |
| 2.003 | H | 4-CH₃ | H | 0 | O | oil |
| 2.004 | F | 4-CH₃ | H | 0 | O | oil |
| 2.005 | H | 4-CH₂CH₃ | H | 0 | O | |
| 2.006 | F | 4-CH₂CH₃ | H | 0 | O | |
| 2.007 | H | 4-(CH₂)₂CH₃ | H | 0 | O | |
| 2.008 | F | 4-(CH₂)₂CH₃ | H | 0 | O | |
| 2.009 | H | 4-CH(CH₃)₂ | H | 0 | O | |
| 2.010 | F | 4-CH(CH₃)₂ | H | 0 | O | |
| 2.011 | H | 4-CH₂Cl | H | 0 | O | |
| 2.012 | F | 4-CH₂Cl | H | 0 | O | |
| 2.013 | H | 4-CH₂Br | H | 0 | O | |
| 2.014 | F | 4-CH₂Br | H | 0 | O | |
| 2.015 | H | 4-CH₂CN | H | 0 | O | |
| 2.016 | F | 4-CH₂CN | H | 0 | O | |
| 2.017 | H | 4-CH₂OH | H | 0 | O | 91–93 |
| 2.018 | F | 4-CH₂OH | H | 0 | O | |
| 2.019 | H | 4-CH₂SH | H | 0 | O | |
| 2.020 | F | 4-CH₂SH | H | 0 | O | |
| 2.021 | H | 4-CH₂CO₂CH₃ | H | 0 | O | |
| 2.022 | F | 4-CH₂CO₂CH₃ | H | 0 | O | |
| 2.023 | H | 4-CH₂CO₂CH₂CH₃ | H | 0 | O | |
| 2.024 | F | 4-CH₂CO₂CH₂CH₃ | H | 0 | O | |
| 2.025 | H | 4-CH₂OCH₃ | H | 0 | O | |
| 2.026 | F | 4-CH₂OCH₃ | H | 0 | O | |
| 2.027 | H | 4-CH₂OCH₂CH₃ | H | 0 | O | |
| 2.028 | F | 4-CH₂OCH₂CH₃ | H | 0 | O | |
| 2.029 | H | 4-CH₂SCH₃ | H | 0 | O | |
| 2.030 | F | 4-CH₂SCH₃ | H | 0 | O | |
| 2.031 | H | 4-CH₂CH₂SCH₃ | H | 0 | O | |
| 2.032 | F | 4-CH₂CH₂SCH₃ | H | 0 | O | |
| 2.033 | H | 4-CH₂OCH₂CH=CH₂ | H | 0 | O | |
| 2.034 | F | 4-CH₂OCH₂CH=CH₂ | H | 0 | O | |
| 2.035 | H | 4-CH₂OCH₂C≡CH | H | 0 | O | |
| 2.036 | F | 4-CH₂OCH₂C≡CH | H | 0 | O | |
| 2.037 | H | 4-CH₂OCOCH₃ | H | 0 | O | |
| 2.038 | F | 4-CH₂OCOCH₃ | H | 0 | O | |
| 2.039 | H | 4-CH₂OCOCH₂CH₃ | H | 0 | O | |
| 2.040 | F | 4-CH₂OCOCH₂CH₃ | H | 0 | O | |
| 2.041 | H | 4-CO₂CH₃ | H | 0 | O | |
| 2.042 | F | 4-CO₂CH₃ | H | 0 | O | |
| 2.043 | H | 4-CO₂CH₂CH₃ | H | 0 | O | |
| 2.044 | F | 4-CO₂CH₂CH₃ | H | 0 | O | |
| 2.045 | H | 4-COOH | H | 0 | O | |
| 2.046 | F | 4-COOH | H | 0 | O | |
| 2.047 | H | 4-CH₂SCH₂CO₂CH₃ | H | 0 | O | |
| 2.048 | F | 4-CH₂SCH₂CO₂CH₃ | H | 0 | O | |
| 2.049 | H | 4-CH₂SCH₂CO₂CH₂CH₃ | H | 0 | O | |
| 2.050 | F | 4-CH₂SCH₂CO₂CH₂CH₃ | H | 0 | O | |
| 2.051 | H | 4-CH₂OCH₂CO₂CH₃ | H | 0 | O | |

TABLE 2-continued

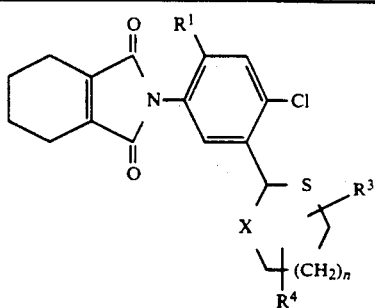

| No. | R¹ | R³ | R⁴ | n | X | mp. [°C.] |
|---|---|---|---|---|---|---|
| 2.052 | F | 4-CH₂OCH₂CO₂CH₃ | H | 0 | O | |
| 2.053 | H | 4-CH₂OCH₂CO₂CH₂CH₃ | H | 0 | O | |
| 2.054 | F | 4-CH₂OCH₂CO₂CH₂CH₃ | H | 0 | O | |
| 2.055 | H | 4-CH₃ | 5-CH₃ | 0 | O | |
| 2.056 | F | 4-CH₃ | 5-CH₃ | 0 | O | |
| 2.057 | H | H | 5-CH₃ | 0 | O | |
| 2.058 | F | H | 5-CH₃ | 0 | O | |
| 2.059 | H | H | 5-CH₂CH₃ | 0 | O | |
| 2.060 | F | H | 5-CH₂CH₃ | 0 | O | |
| 2.061 | H | H | 5-(CH₂)₂CH₃ | 0 | O | |
| 2.062 | F | H | 5-(CH₂)₂CH₃ | 0 | O | |
| 2.063 | H | H | 5-CH(CH₃)₂ | 0 | O | |
| 2.064 | F | H | 5-CH(CH₃)₂ | 0 | O | |
| 2.065 | H | 5-CH₂Cl | H | 0 | O | |
| 2.066 | F | 5-CH₂Cl | H | 0 | O | |
| 2.067 | H | 5-CH₂Br | H | 0 | O | |
| 2.068 | F | 5-CH₂Br | H | 0 | O | |
| 2.069 | H | 5-CH₂CN | H | 0 | O | |
| 2.070 | F | 5-CH₂CN | H | 0 | O | |
| 2.071 | H | 5-CH₂OH | H | 0 | O | |
| 2.072 | F | 5-CH₂OH | H | 0 | O | |
| 2.073 | H | 5-CH₂SH | H | 0 | O | |
| 2.074 | F | 5-CH₂SH | H | 0 | O | |
| 2.075 | H | 5-CH₂CO₂CH₃ | H | 0 | O | |
| 2.076 | F | 5-CH₂CO₂CH₃ | H | 0 | O | |
| 2.077 | H | 5-CH₂CO₂CH₂CH₃ | H | 0 | O | |
| 2.078 | F | 5-CH₂CO₂CH₂CH₃ | H | 0 | O | |
| 2.079 | H | 5-CH₂OCH₃ | H | 0 | O | |
| 2.080 | F | 5-CH₂OCH₃ | H | 0 | O | |
| 2.081 | H | 5-CH₂OCH₂CH₃ | H | 0 | O | |
| 2.282 | F | 5-CH₂OCH₂CH₃ | H | 0 | O | |
| 2.083 | H | 5-CH₂SCH₃ | H | 0 | O | |
| 2.084 | F | 5-CH₂SCH₃ | H | 0 | O | |
| 2.085 | H | 5-CH₂OCH₂CH=CH₂ | H | 0 | O | |
| 2.086 | F | 5-CH₂OCH₂CH=CH₂ | H | 0 | O | |
| 2.087 | H | 5-CH₂OCH₂C≡CH | H | 0 | O | |
| 2.088 | F | 5-CH₂OCH₂C≡CH | H | 0 | O | |
| 2.089 | H | 5-CH₂OCOCH₃ | H | 0 | O | |
| 2.090 | F | 5-CH₂OCOCH₃ | H | 0 | O | |
| 2.091 | H | 5-CH₂OCOCH₂CH₃ | H | 0 | O | |
| 2.092 | F | 5-CH₂OCOCH₂CH₃ | H | 0 | O | |
| 2.093 | H | 5-CO₂CH₃ | H | 0 | O | |
| 2.094 | F | 5-CO₂CH₃ | H | 0 | O | |
| 2.095 | H | 5-CO₂CH₂CH₃ | H | 0 | O | |
| 2.096 | F | 5-CO₂CH₂CH₃ | H | 0 | O | |
| 2.097 | H | 5-COOH | H | 0 | O | |
| 2.098 | F | 5-COOH | H | 0 | O | |
| 2.099 | H | 5-CH₂SCH₂CO₂CH₃ | H | 0 | O | |
| 2.100 | F | 5-CH₂SCH₂CO₂CH₃ | H | 0 | O | |
| 2.101 | H | 5-CH₂SCH₂CO₂CH₂CH₃ | H | 0 | O | |
| 2.102 | F | 5-CH₂SCH₂CO₂CH₂CH₃ | H | 0 | O | |
| 2.103 | H | 5-CH₂OCH₂CO₂CH₃ | H | 0 | O | |
| 2.104 | F | 5-CH₂OCH₂CO₂CH₃ | H | 0 | O | |
| 2.105 | H | 5-CH₂OCH₂CO₂CH₃ | H | 0 | O | |
| 2.106 | F | 5-CH₂OCH₂CO₂CH₃ | H | 0 | O | |

TABLE 3

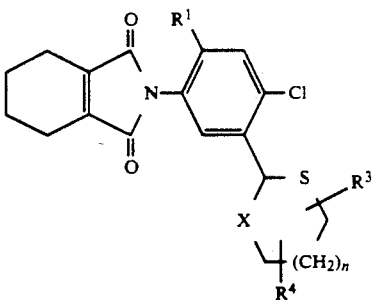

| No. | R¹ | R³ | R⁴ | n | X | mp. [°C.] |
|---|---|---|---|---|---|---|
| 3.001 | H | H | H | 1 | S | 198–200 |
| 3.002 | F | H | H | 1 | S | |
| 3.003 | H | 4-CH₃ | H | 1 | S | 158–159 |
| 3.004 | F | 4-CH₃ | H | 1 | S | |
| 3.005 | H | 4-CH₂CH₃ | H | 1 | S | |
| 3.006 | F | 4-CH₂CH₃ | H | 1 | S | |
| 3.007 | H | 4-(CH₂)₂CH₃ | H | 1 | S | |
| 3.008 | F | 4-(CH₂)₂CH₃ | H | 1 | S | |
| 3.009 | H | 4-CH(CH₃)₂ | H | 1 | S | |
| 3.010 | F | 4-CH(CH₃)₂ | H | 1 | S | |
| 3.011 | H | 4-CH₂Cl | H | 1 | S | |
| 3.012 | F | 4-CH₂Cl | H | 1 | S | |
| 3.013 | H | 4-CH₂Br | H | 1 | S | |
| 3.014 | F | 4-CH₂Br | H | 1 | S | |
| 3.015 | H | 4-CH₂CN | H | 1 | S | |
| 3.016 | F | 4-CH₂CN | H | 1 | S | |
| 3.017 | H | 4-CH₂OH | H | 1 | S | |
| 3.018 | F | 4-CH₂OH | H | 1 | S | |
| 3.019 | H | 4-CH₂SH | H | 1 | S | |
| 3.020 | F | 4-CH₂SH | H | 1 | S | |
| 3.021 | H | 4-CH₂CO₂CH₃ | H | 1 | S | |
| 3.022 | F | 4-CH₂CO₂CH₃ | H | 1 | S | |
| 3.023 | H | 4-CH₂CO₂CH₂CH₃ | H | 1 | S | |
| 3.024 | F | 4-CH₂CO₂CH₂CH₃ | H | 1 | S | |
| 3.025 | H | 4-CH₂OCH₃ | H | 1 | S | |
| 3.026 | F | 4-CH₂OCH₃ | H | 1 | S | |
| 3.027 | H | 4-CH₂OCH₂CH₃ | H | 1 | S | |
| 3.028 | F | 4-CH₂OCH₂CH₃ | H | 1 | S | |
| 3.029 | H | 4-CH₂SCH₃ | H | 1 | S | |
| 3.030 | F | 4-CH₂SCH₃ | H | 1 | S | |
| 3.031 | H | 4-CH₂CH₂SCH₃ | H | 1 | S | |
| 3.032 | F | 4-CH₂CH₂SCH₃ | H | 1 | S | |
| 3.033 | H | 4-CH₂OCH₂CH=CH₂ | H | 1 | S | |
| 3.034 | F | 4-CH₂OCH₂CH=CH₂ | H | 1 | S | |
| 3.035 | H | 4-CH₂OCH₂C≡CH | H | 1 | S | |
| 3.036 | F | 4-CH₂OCH₂C≡CH | H | 1 | S | |
| 3.037 | H | 4-CH₂OCOCH₃ | H | 1 | S | |
| 3.038 | F | 4-CH₂OCOCH₃ | H | 1 | S | |
| 3.039 | H | 4-CH₂OCOCH₂CH₃ | H | 1 | S | |
| 3.040 | F | 4-CH₂OCOCH₂CH₃ | H | 1 | S | |
| 3.041 | H | 4-CO₂CH₃ | H | 1 | S | |
| 3.042 | F | 4-CO₂CH₃ | H | 1 | S | |
| 3.043 | H | 4-CO₂CH₂CH₃ | H | 1 | S | |
| 3.044 | F | 4-CO₂CH₂CH₃ | H | 1 | S | |
| 3.045 | H | 4-COOH | H | 1 | S | |
| 3.046 | F | 4-COOH | H | 1 | S | |
| 3.047 | H | 4-CH₂SCH₂CO₂CH₃ | H | 1 | S | |
| 3.048 | F | 4-CH₂SCH₂CO₂CH₃ | H | 1 | S | |
| 3.049 | H | 4-CH₂SCH₂CO₂CH₂CH₃ | H | 1 | S | |
| 3.050 | F | 4-CH₂SCH₂CO₂CH₂CH₃ | H | 1 | S | |
| 3.051 | H | 4-CH₂OCH₂CO₂CH₃ | H | 1 | S | |
| 3.052 | F | 4-CH₂OCH₂CO₂CH₃ | H | 1 | S | |
| 3.053 | H | 4-CH₂OCH₂CO₂CH₂CH₃ | H | 1 | S | |
| 3.054 | F | 4-CH₂OCH₂CO₂CH₂CH₃ | H | 1 | S | |
| 3.055 | H | 4-CH₃ | 6-CH₃ | 1 | S | |
| 3.056 | F | 4-CH₃ | 6-CH₃ | 1 | S | |
| 3.057 | H | 5-CH₃ | 5-CH₃ | 1 | S | |
| 3.058 | F | 5-CH₃ | 5-CH₃ | 1 | S | |

TABLE 4

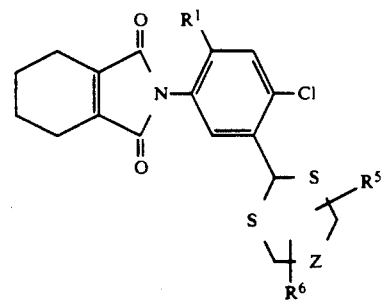

| No. | R¹ | R⁵ | R⁶ | Z | mp. [°C.] |
|---|---|---|---|---|---|
| 4.001 | H | H | H | —CH=CH— | |
| 4.002 | F | H | H | —CH=CH— | |
| 4.003 | H | 4-CH₃ | H | —CH=CH— | |
| 4.004 | F | 4-CH₃ | H | —CH=CH— | |
| 4.005 | H | 4-CH₂CH₃ | H | —CH=CH— | |
| 4.006 | F | 4-CH₂CH₃ | H | —CH=CH— | |
| 4.007 | H | 4-CH₂CH₂CH₃ | H | —CH=CH— | |
| 4.008 | F | 4-CH₂CH₂CH₃ | H | —CH=CH— | |
| 4.009 | H | 4-CH(CH₃)₂ | H | —CH=CH— | |
| 4.010 | F | 4-CH(CH₃)₂ | H | —CH=CH— | |
| 4.011 | H | 4-CH₃ | 7-CH₃ | —CH=CH— | |
| 4.012 | F | 4-CH₃ | 7-CH₃ | —CH=CH— | |
| 4.013 | H | H | H | —CH₂OCH₂— | 134–135 |
| 4.014 | F | H | H | —CH₂OCH₂— | |
| 4.015 | H | 4-CH₃ | H | —CH₂OCH₂— | |
| 4.016 | F | 4-CH₃ | H | —CH₂OCH₂— | |
| 4.017 | H | 4-CH₂CH₃ | H | —CH₂OCH₂— | |
| 4.018 | F | 4-CH₂CH₃ | H | —CH₂OCH₂— | |
| 4.019 | H | 4-CH₂CH₂CH₃ | H | —CH₂OCH₂— | |
| 4.020 | F | 4-CH₂CH₂CH₃ | H | —CH₂OCH₂— | |
| 4.021 | H | 4-CH(CH₃)₂ | H | —CH₂OCH₂— | |
| 4.022 | F | 4-CH(CH₃)₂ | H | —CH₂OCH₂— | |
| 4.023 | H | 4-CH₃ | 8-CH₃ | —CH₂OCH₂— | |
| 4.024 | F | 4-CH₃ | 8-CH₃ | —CH₂OCH₂— | |
| 4.025 | H | H | H | —CH₂SCH₂— | |
| 4.026 | F | H | H | —CH₂SCH₂— | |
| 4.027 | H | 4-CH₃ | H | —CH₂SCH₂— | |
| 4.028 | F | 4-CH₃ | H | —CH₂SCH₂— | |
| 4.029 | H | 4-CH₂CH₃ | H | —CH₂SCH₂— | |
| 4.030 | F | 4-CH₂CH₃ | H | —CH₂SCH₂— | |
| 4.031 | H | 4-CH₂CH₂CH₃ | H | —CH₂SCH₂— | |
| 4.032 | F | 4-CH₂CH₂CH₃ | H | —CH₂SCH₂— | |
| 4.033 | H | 4-CH(CH₃)₂ | H | —CH₂SCH₂— | |
| 4.034 | F | 4-CH(CH₃)₂ | H | —CH₂SCH₂— | |
| 4.035 | H | 4-CH₃ | 8-CH₃ | —CH₂SCH₂— | |
| 4.036 | F | 4-CH₃ | 8-CH₃ | —CH₂SCH₂— | |

TABLE 5

| No. | R¹ | R³ | R⁴ | X | mp. [°C.] |
|---|---|---|---|---|---|
| 5.001 | H | H | H | S | |
| 5.002 | F | H | H | S | 104–106 |
| 5.003 | H | CH₃ | H | S | |
| 5.004 | F | CH₃ | H | S | 110–112 |
| 5.005 | H | H | H | O | |
| 5.006 | F | H | H | O | |
| 5.007 | H | CH₃ | H | O | |
| 5.008 | F | CH₃ | H | O | oil |

The herbicidal agents, or the active ingredients on which they are based, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.005 to 3.0, preferably 0.01 to 0.5, kg/ha.

The action of the active ingredients of the formula I on the growth of plants is illustrated in greenhouse experiments.

The vessels employed were plastic flowerpots having a volume of 300 cm$^3$ and filled with a sandy loam containing about 3.0% humus. The seeds of the test plants were sown separately, according to species.

For the postemergence treatment, either plants which had been sown in the pots and grown there were selected, or they were cultivated separately as seedlings and transplanted to the pots a few days before being treated.

Depending on growth form, the plants were grown to a height of from 3 to 15 cm before being treated with the active ingredients which were suspended or emulsified in water and sprayed through finely distributing nozzles. The application rates for postemergence treatment were 0.015 and 0.03 kg/ha.

The pots were set up in the greenhouse, species from warmer climates in warmer areas (20° to 36° C.) and species from moderate climates at 10° to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments belonged to the following species:

| CODE | Botanical name | Common name |
| --- | --- | --- |
| ABUTH | Abutilon theophrasti | velvet leaf |
| AMARE | Amaranthus spp. | pigweed |
| CHYCO | Chrysanthemum corinarium | crown daisy |
| DEDTO | Desmodium tortuosum | Florida beggarweed |
| GALAP | Galium aparine | catchweed bedstraw |
| IPOSS | Ipomoea spp. | morningglory |
| LAMAM | Lamium amplexicaule | henbit |
| MERAN | Mercurialis annua | annual mercury |
| SOLNI | Solanum nigrum | black nightshade |
| STEME | Stellaria media | chickweed |
| TRZAS | Triticum aestivum | spring wheat |
| ZEAMX | Zea mays | Indian corn |

In view of the numerous application methods possible, the compounds according to the invention, or agents containing them, may be used in a large number of crop plants for removing unwanted plants. The following crops are examples:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgairs spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | panic grass |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, |

| Botanical name | Common name |
|---|---|
| | sweet corn, maize |

To increase the spectrum of action and to achieve synergistic effects, the N-phenyltetrahydrophthalimides of the formula I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acids and salts, esters and amides thereof, etc.

It may also be useful to apply the N-phenyltetrahydrophthalimides of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

TABLE 6

Herbicidal action and tolerance by a crop on postemergence application of 0.03 kg/ha of compound no. 1.001 in the greenhouse

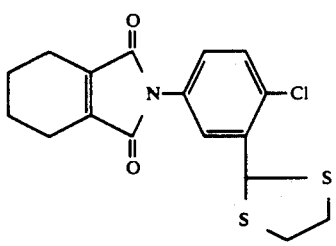

comp. no. 1.001

| Test plants | Damage (%) |
|---|---|
| TRZAS | 0 |
| AMARE | 100 |
| GALAP | 100 |
| IPOSS | 100 |
| MERAN | 100 |

TABLE 7

Herbicidal action on postemergence application of compound no. 1.003 at a rate of 0.03 kg/ha in the greenhouse

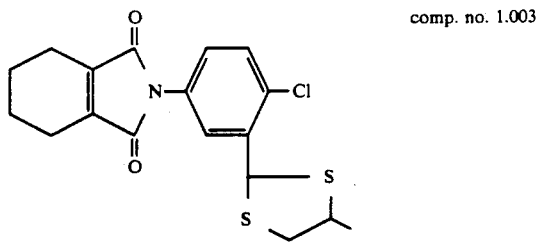

comp. no. 1.003

| Test plants | Damage (%) |
|---|---|
| ABUTH | 100 |
| AMARE | 100 |
| DEDTO | 100 |
| GALAP | 100 |
| IPOSS | 100 |
| MERAN | 100 |
| SOLNI | 100 |
| STEME | 100 |

TABLE 8

Control of unwanted broadleaved plants and tolerance by a crop on postemergence application of 0.015 kg/ha in the greenhouse

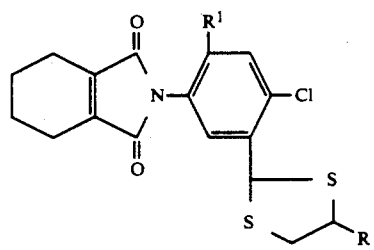

| Comp. no. | $R^1$ | R | ZEAMX | CHYCO | GALAP | LAMAM | SOLNI | STEME |
|---|---|---|---|---|---|---|---|---|
| 1.002 | F | H | 10 | 100 | 100 | 100 | 100 | 100 |
| 1.003 | F | $CH_3$ | 15 | 100 | 100 | 100 | 100 | 100 |

We claim:

1. An N-phenyltetrahydrophthalimide of the formula I:

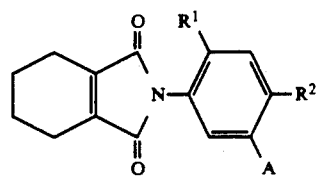

wherein $R^1$ is hydrogen or halogen, $R^2$ is halogen, A is a substituent of the formula:

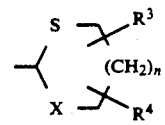

-continued

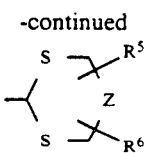

wherein X is oxygen or sulfur; n is 0 or 1; $R^3$ is hydrogen or $C_1$-$C_6$-alkoxycarbonyl or $C_1$-$C_3$-alkyl which is unsubstituted or substituted by halogen, cyano, hydroxy, mercapto, $C_1$-$C_6$-alkoxycarbonyl, $C_1$-$C_4$-alkoxy, $C_1$-$C_4$-alkylthio, $C_3$-$C_6$-alkenyloxy, $C_3$-$C_6$-alkenylthio, $C_3$-$C_6$-alkynyloxy, $C_3$-$C_6$-alkynylthio or $C_1$-$C_4$-acyloxy, or is hydroxy or carboxy or is $C_1$-$C_4$-alkoxy-$C_1$-$C_2$-alkyl or $C_1$-$C_4$-alkylthio-$C_1$-$C_2$-alkyl which is unsubstituted or substituted in the alkylether or thioether moiety by $C_1$-$C_6$-alkoxycarbonyl; $R^4$ is hydrogen or $C_1$-$C_3$-alkyl; Z is methyleneoxymethylene, methylenethiomethylene or ethenylene; $R^5$ is hydrogen or $C_1$-$C_3$-alkyl; and $R^6$ is hydrogen or $C_1$-$C_3$-alkyl, independently of the steric configuration, with the proviso that n is 1 when $R^3$ and $R^4$ are both hydrogen.

2. The N-phenyltetrahydrophthalimide of claim 1, wherein $R^1$ is hydrogen or fluorine, $R^2$ is chlorine and A is dithiolane or oxathiolane rings, which are unsubstituted or substituted.

3. The N-phenyltetrahydronaphthalimide of claim 1, wherein A is

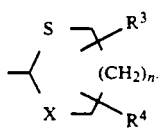

4. The N-phenyltetrahydronaphthalimide of claim 1, wherein A is

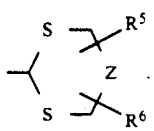

5. The compound of claim 2 having the formula:

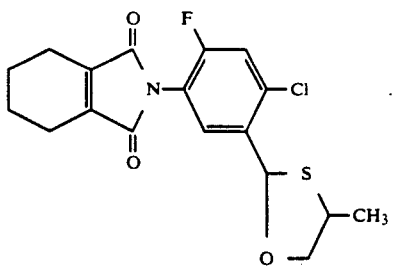

6. A compound according to claim 2 wherein $R^1$ is H, $R^2$ is chloro, and A is

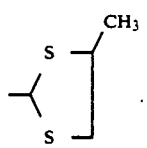

7. A compound according to claim 2 wherein $R^1$ is F, $R^2$ is Cl, and A is

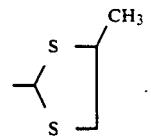

8. A compound according to claim 2 wherein $R^1$ is H, $R^2$ is Cl, and A is

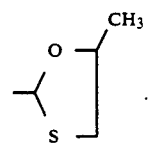

9. A compound according to claim 2, wherein $R^1$ is F, $R^2$ is F, and A is

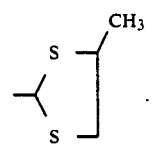

10. A compound according to claim 2 wherein $R^1$ is F, $R^2$ is F, and A is

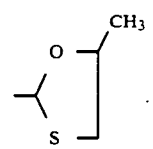

11. A compound according to claim 2 having the formula:

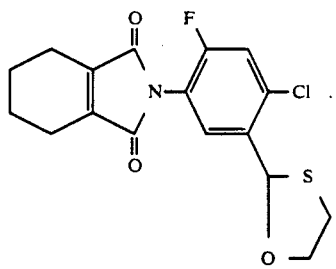

12. A herbicidal agent, comprising an effective amount of one or more compounds of the formula I as set forth in claim 4, and one or more auxiliaries, extenders or diluents.

13. The herbicidal agent of claim 12, wherein for the compound of the formula I, $R^1$ is hydrogen or fluorine, $R^2$ is chlorine and A is dithiolane or oxathiolane rings, which are unsubstituted or substituted.

14. A process for combating the growth of unwanted plants, which comprises applying to said plants or their habitat or both a herbicidally effective amount of one or more N-phenyltetrahydrophthalimide compounds of the formula I as set forth in claim 1.

15. The process of claim 14, wherein for the compound of the formula I, $R^1$ is hydrogen or fluorine, $R^2$ is chlorine and A is dithiolane or oxothiolane rings, which are unsubstituted or substituted.

16. The process of claim 14, wherein said herbicidally effective amount is from about 0.005-3.0 kg/ha.

17. The process of claim 16, wherein said herbicidally effective amount is from about 0.01-0.5 kg/ha.

18. The process of claim 16, wherein said herbicidally effective amount is from about 0.015-0.03 kg/ha for post-emergence treatment.

* * * * *